United States Patent [19]

Sachse et al.

[11] Patent Number: 4,592,034

[45] Date of Patent: May 27, 1986

[54] ACOUSTIC EMISSION SOURCE LOCATION ON PLATE-LIKE STRUCTURES USING A SMALL ARRAY OF TRANSDUCERS

[75] Inventors: Wolfgang H. Sachse, Ithaca, N.Y.; Selcuk Sancar, Columbus, Ohio

[73] Assignee: Cornell Research Foundation, Inc., Ithaca, N.Y.

[21] Appl. No.: 441,986

[22] Filed: Nov. 15, 1982

[51] Int. Cl.$^4$ .......................... G01D 7/00; G01S 3/80
[52] U.S. Cl. .................................... 367/127; 73/587; 367/129
[58] Field of Search ............... 367/117, 127, 902, 118, 367/123, 129, 907; 73/827, 587; 343/417, 419, 450, 458, 463, 465

[56] References Cited

U.S. PATENT DOCUMENTS

| | | | |
|---|---|---|---|
| 3,723,960 | 3/1973 | Harris | 367/127 |
| 3,725,855 | 4/1973 | Murphree et al. | 367/127 |
| 3,822,586 | 7/1974 | Pollock | 73/587 |
| 3,858,439 | 1/1975 | Nakamura | 73/658 |
| 3,875,381 | 4/1975 | Wingfield et al. | 73/587 |
| 3,890,591 | 6/1975 | Bacquillon et al. | 367/129 |
| 3,914,883 | 10/1975 | Bodine | 37/2 R |
| 3,985,024 | 10/1976 | Horah | 73/587 |
| 4,009,463 | 2/1977 | Vercellotti | 367/127 |
| 4,011,472 | 3/1977 | Feng | 73/587 X |
| 4,033,179 | 7/1977 | Romrell | 73/587 |
| 4,037,189 | 7/1977 | Bell et al. | 367/127 |
| 4,088,907 | 5/1978 | Jones et al. | 73/587 |
| 4,268,712 | 5/1981 | Overall | 174/17.08 |
| 4,309,903 | 1/1982 | Ono | 73/587 |
| 4,481,818 | 11/1984 | Hellquist | 73/587 |
| 4,506,354 | 3/1985 | Hansen | 367/907 X |

OTHER PUBLICATIONS

Golinelli, S., A Minicomputer in an Acoustic Emission Source Location System, 12/75.
McElroy, Acoustic Emissions of Buried Pipelines, Acoustic Emission Monitoring of Pressurized Sys., ASTM STP 697, ASTM (1979), pp. 47–59.
Tatro et al., On-Line Safety Monitoring of a Large High Pressure, High Temp. Autoclave, Acous. Emission Monitoring of Press. Sys., ASTM STP 697, ASTM (1979).
Hutton et al., Acous. Emission Meas.: HSST V-7B Intermediate Vessel Test, Acous. Emission Monitoring of Press. Sys., ASTM STP 697, ASTM (1979), pp. 106–130.
Voltava et al., Inspec. of Nuclear Reac. by Means of Acous. Emission During Hydro. Test., Acous. Emiss. Monit. of Press. Sys., ASTM STP 697, ASTM (1979).
Nakosa, Instru. and Signal Proc. for Monit. Struc. Integrity by Acous. Emiss., Proc. Int'l. Conference on Acous. Emiss., Anaheim, Cal., 1979, pp. 65–86.
Tomaguchi et al., Acous. Emiss. Source Location by Ident. and Comb. of Signals, Proc. Int'l. Conf. on Acous. Emiss., Anahein, Cal., 1979, pp. 49–64.

(List continued on next page.)

*Primary Examiner*—Charles T. Jordan
*Assistant Examiner*—Brian S. Steinberger
*Attorney, Agent, or Firm*—Jones, Tullar & Cooper

[57] ABSTRACT

A small non-colinear transducer array for omnidirectional acoustic emission monitoring is disclosed. The small transducer array consists of four piezoelectric sensor elements of sufficiently small diameter as to function as essentially point receivers and of sufficient frequency response as to be sensitive to the signals to be detected. The sensor elements of the transducer array are close together and are non-colinear so that the signals received by them can be used for determining the group velocity of acoustic waves on solid plates and on plate-like structures such as shells and pipes, and to permit determination of both the source direction and distance. The array is designed to monitor the region exterior to the area enclosed by the array, and the ratio of the smallest distance between sensors to the radius of a single transducer element is relatively large in order to minimize measurement errors introduced by undertainties in transducer element positions caused by large transducer sizes with respect to the acoustic waves being received.

17 Claims, 5 Drawing Figures

OTHER PUBLICATIONS

Nakasa et al., Development of a Multichannel Acous. Emiss. Instru. Sys. for Field Applns., Proc. The 5th Acous. Emiss. Symposium, Tokyo, 1980, pp. 327–338.

Hatano et al., Acous. Emiss. Source Location Using Face-Centered Trans. Arrays, J. of Elec. and Comm. in Japan, vol. 61, No. 10, 1978, pp. 97–104.

Tobias, Acous. Emiss. Source Location in Two Dimensions by an Array of Three Sensors, Nondestructive Testing, Feb. 1976, pp. 9–12.

Asty, Acous. Emiss. Source Location on a Spherical or Plane Surface, Non-Destructive Testing Int'l., Oct. 1978, pp. 223–226.

Pao, Theory of Acous. Emiss., in Elastic Waves and Non-Destructive Testing of Materials, AMD, vol. 29, Y. H. Pao. Ed., ASME, N.Y. (1978), pp. 107–128.

Rundorf, Acous. Emiss. Source Location in Theory and Practice, Proc., The 5th Int'l. Acous. Emiss. Symposium, Tokyo, 1980, pp. 91–102.

Rundorf, Location of Microseismic Activity, Proc. . . . , Int'l. Conf. on . . . Microseismic Activity, 1981.

Carter, Time Delay Estimation for Passive Sonar Signal Proc., Trans. IEEE on Acous., Speech & Signal Proc., Part II of 3 Parts, Spec. Issue on Time Delay Estimation, vol. 1, ASSP-29, No. 3, 1981, pp. 463–470.

Carter, Passive Ranging Errors Due to Receiving Hydrophone Position Uncertainty, J. Acous. Soc. Am., vol. 65, No. 2, 1979, pp. 528–530.

Sackman, The Use of Phase-Difference Trace Func. for Bearing Estimation with Small Arrays, In Reference 14, pp. 501–507.

Kirlin et al., Improvement of Delay Measurements Fron Sonar Arrays Via Sequential State Estimation, In Reference 14, pp. 514–578.

Clay et al., Use of a Two Dimensional Array to Receive an Unknown Signal in a Dispensive Waveguide, J. Acous. Soc. Am., vol. 47, 2/70, pp. 435–444.

Clay et al., Error Analysis of Velocity and Direction Meas. of Plane Waves Using Trick Large Aperture Arrays, J. Acous. Soc. Am., vol. 53, 4/73, pp. 1161–1166.

Sachse et al., Signals in the Far-Field of an AE Source, Ultrasonics Int'l. 1981: Conf. Proc., IPC Science & Tech. Press., Guilford, England (1979) in press.

Weaver et al., Axisymmetric Elas. Waves Excited by a Point Source in a Plate. Part I. Theory . . . in Normal Modes, J. Appl. Mech., 1981 (to appear).

Courant et al., Method of Mathematical Physics, vol. I, p. 36.

Weaver et al., Axisymmetric Elastic Waves Excited by a Point Source in a Plate, Part II, Surface Responses, J. Appl. Mech., 1981 (to appear).

ACOUSTIC EMISSION SOURCE LOCATION ON PLATE-LIKE STRUCTURES USING A SMALL ARRAY OF TRANSDUCERS

The invention described herein was made in the course of work under grant numbers DMR-79-24008-A03 and ENG79-10311 from the National Science Foundation.

The present invention relates, in general, to a method and apparatus for determining the distance and direction of a source of acoustic emission, and more particularly to a transducer array for making such determinations on solid plates and plate-like structures such as pipes and shells, the array being extremely small and being designed to monitor the region exterior to the area within the array.

The location of an acoustic source emitting a propagating disturbance in the form of an acoustic wave, whether in the atmosphere, under water, under the earth's crust, inside a structural element, or the like, can be determined in accordance with known techniques by geometrical triangulation techniques. Such determinations are made with respect to a number of fixed points which receive the disturbance through the simple application of plane or spherical triangulation equations. The mathematics of source location in accordance with such techniques is simply a matter of the simultaneous solution of such equations, one for each pair of fixed points, as long as the differences in length between the two sides of a triangle can be measured using the information recorded at the fixed receiver points.

Although such a geometrical approach to the location of an acoustic source is appealing in its simplicity, such a geometrical construction requires a number of assumptions, none of which is exactly satisfied in the physical applications of such techniques to wave propagation in areas such as seismology, the monitoring of microseismic activity, passive sonar, and acoustic emission detection. The assumptions involved are that all sources and receivers are points; that the receiver locations are fixed and are precisely known; that the medium is homogenous so that there is a single speed of propagation and the path from the source to a receiver is unbroken; and that the difference in length between two legs of a triangle, which is the phase difference, has been measured exactly. Even when these conditions are assumed to be satisfied, and a solution is constructed using a particular array geometry, the solution may not be unique or there may be no solution at all. Accordingly, in practical applications, difficulties are encountered in obtaining a close estimate of source location variables.

In acoustic emission applications, where, for example, the structural integrity of pressure vessels, reactors, or other plate-like structures is to be monitored, the major concern in prior art systems has been to determine the single wave propagation velocity to be used, and from this to determine the optimal geometry of the receiver array. In addition, sophisticated electronic instrumentation must be designed to identify the correct feature of the received waveform which is to be associated with the chosen velocity of propagation, and such instrumentation must be capable of measuring the relative arrival time with extreme precision at all of the array points. Once the velocity and time delays are measured, theoretical formulations appropriate to the structure and array geometry are used to obtain the source location.

In such systems, the determination of a particular velocity of propagation is done by a precalibration procedure where, after the array is placed on the structure, an artificial source is activated at a known location. Then time delays of a selected wave form feature are measured, and knowing the location of the source and of the receivers, these time delays are used to derive the velocity of propagation. In the subsequent actual monitoring of the structure, received emissions are analyzed to identify the same wave form feature by which the calibration was made. Such features may, for example, be the first-arrival P-wave or the Rayleigh surface wave.

Due to the dispersive wave propagation in a structure and because of possible inhomogeneities in that structure, however, there is no accurate way to calibrate such a system to the actual wave propagation mode and velocity by such a use of an artificial source. See "Acoustic Emissions of Buried Pipelines", J. W. McElroy, *Acoustic Emission Monitoring of Pressurized Systems* ASTM STP 697, ASTM (1979) pages 47–59. Further, as pointed out by C. A. Tatro et al, "On-Line Safety Monitoring of a Large High Pressure, High Temperature Autoclave", *Acoustic Emission Monitoring of Pressurized Systems,* ASTM STP 697, ASTM (1979) pages 70–90, the value of the sound velocity derived from various calibration sources is not relatable in a simple way to any of the pure modes normally used to describe sound transmission in solids. Thus, the prior art use of a particular velocity for precalibration of a monitoring system has not proved to be a successful approach in acoustic emission source location.

A further difficulty has been encountered in the use of large arrays of widely separated transducers which normally are placed as symmetrically as possible so that the equations to be solved are simplified. The choice of the large array is prompted by the fact that with a given source location, the phase difference in waveforms arriving at various receiver elements will be large enough to be easily measured and distinct enough to differentiate various source locations. However, as is the case with the use of artificial sources for velocity calibration, the dispersion or distortion of the waves to be measured as they pass through the array creates various problems. Thus, the larger the array, the more the received waveforms will be distorted as they move from one receiver location to another, making proper identification of wave features difficult. Further, when the transducer elements are widely separated, each received waveform is more likely to be differently affected by inhomogeneities in the material.

Another problem encountered in prior systems arises from the use of large diameter transducers in a large array, for such transducers introduce the problem of uncertainty in the receiver location. The transducer will provide a response representing the average signal received across its area, and where accurate measurements are to be made, such averaging produces adverse effects in the determination of source location.

From the foregoing, it is apparent that even though the theory of wave propagation in plates and plate-like structures has been extensively studied, the theoretical results cannot be utilized in actual practice for the accurate location of acoustic emission sources for three reasons. First, precalibration of the acoustic emission system is required for velocity determination. Since such precalibration must be done with a particular mode arrival, it may not be valid for use in actual practice, since the modes produced at a receiver by an artificial source at a known arbitrary location may not be present in the actual acoustic emission being measured. Secondly, the acoustic emission detecting systems widely used at the present time operate on threshold-level-cross at the first arrival of the waveform, and a normal mode analysis is not done. Thirdly, since the arrays used in prior systems are large, there is substantial dispersion of the waveform over the array so that a particular mode structure present in a waveform reaching one transducer element may not be identifiable at another transducer element.

SUMMARY OF THE INVENTION

It is, therefore, an object of the present invention to provide a transducer array which is adapted to provide accurate measurements of the direction and distance of a source of acoustic emissions.

It is a further object of the present invention to provide a transducer array adapted to respond to a selected wave feature, whereby the direction and distance to the source of the wave form can be determined without the need for measuring predetermined wave features and without the need for prior calibration of the array.

It is another object of the invention to provide a small transducer array for monitoring the region exterior to the array to determine the direction and distance of an acoustic emission source without prior system calibration and through the use of any selected waveform feature.

Another object of the invention is the use of a small transducer array for monitoring acoustic emissions, for deriving from the received waveform the source location, and for group velocity determination on solid plates and plate-like structures such as pipes and shells, whereby both source direction and distance can be determined.

The effectiveness of the small transducer array disclosed herein is based on the recognition that propagating waveforms change in shape substantially as they travel through a solid material. These changes are caused by a variety of factors, but it has been found that by arranging the transducers very close together so that the maximum array dimension is equal to or less than a wave length of the signal to be measured, measurements of wave characteristics can be made before the waveforms change appreciably. By utilizing a plurality of receiver elements, a single feature of the waveform can be detected at each of the stations before that feature is distorted or changed by the propagation medium, and by looking for the same feature at each station, the need for prior calibration of the system is eliminated. Assuming that the material through which the acoustic wave travels has known characteristics, the speed at which various wave modes will travel through that material will also be known. By identifying these specific modes at one or more transducers, the distance to the source can be determined, and an analysis of the time at which each mode reached each of the transducer elements permits a determination of the direction to the source.

In accordance with the present invention, a small, non-colinear, omnidirectional transducer array for acoustic emission monitoring is provided. The transducer array consists of four piezoelectric sensor elements of very small diameter arranged in a non-colinear manner on a solid plate or plate-like structure to monitor the region of the plate exterior to the area within the array to enable the user to determine both direction and distance of a source of acoustic emissions on the plate.

In a preferred form of the invention, each sensor element is approximately 0.067 inch in diameter and the ratio of the smallest distance between any two sensors to the radius of a single sensor is approximately 17.

The four piezoelectric transducers in the array each have a diameter which is much smaller than prior art transducers, and as such, the sensor elements are essentially point receivers. This small size minimizes measurement errors introduced in prior transducer arrays by uncertainties in the receiver position and by the reception of a signal over a relatively large transducer element area.

The array receives acoustic waves propagating directly along the plate as well as waves propagating through the plate and reflecting from its surfaces, each transducer, or sensor element, of the array receiving the waves at a slightly different time. Circuitry is provided to sample the transducers sequentially and to process the received signals in such a manner as to determine the time intervals between arrivals of particular waveform features. For test purposes and to illustrate the concepts of the present invention, a pulse generator may be provided to activate a suitable acoustic signal source on the plate on which the transducer array is placed. The generator may be internally triggered, or may be externally controlled by a time mark generator.

The microprocessor serves to calculate the location of the source of acoustic emissions in accordance with the mathematical relationships disclosed herein. Such calculations may be stored, may be supplied to a data plotter for graphical display, or may be fed to other peripheral equipment for further processing or use.

The transducer array of the present invention is designed mainly to monitor and locate acoustic emission sources outside the area enclosed by imaginary lines connecting the centers of the four transducer elements. This arrangement is contrary to prior art systems wherein acoustic emission source location is done within the boundary defined by the elements of a large array wherein the transducer separations are on the order of several feet. The shape of the array boundary is governed by three specific criteria: First, all receiver elements are not colinear; i.e., the array is not a linear array. Second, the receiver elements are not arranged in a circle and no three receivers in the array are colinear. Third, no pair of receivers in the array lies on a straight line which is parallel to the direction of a straight line defined by the remaining two elements. Accordingly, transducer contact or influence areas are not allowed to overlap, as is the case of beam forming arrays which are often used in underwater applications; i.e., where the signals received by all of the transducer elements in an array are summed.

The spacing between adjacent transducers in the array is dependent on the amount of time it takes to make the required measurements of the wave, for if the elements are too close together, then the measurement takes longer than the time of travel from one transducer to the other, and this will result in all measurements being the same. Thus, the time required for measurement dictates that the elements of the array be spaced apart. However, since accuracy in measurement requires that the same characteristics of the waveform be measured at each transducer, and since the waves change as they travel through the material, it is necessary to have the transducer elements close together so that measurements can be made on a propagating wave before the waveform changes appreciably. The actual spacing of the transducer elements is, therefore, a trade-off between these two opposite requirements.

In a preferred form of the invention, the elements of the array have a maximum spacing of about 1 inch, and thus provide a maximum arrival time delay of 5 microseconds between the receipt of a waveform at a first element of the array and the receipt of the same characteristics of the waveform at another element of the array. Thus, the maximum array dimension is less than or on the order of the wave length to be received.

The source location is determined by considering the arrival time differences between the received signals at each of the stations in the array, taken in conjunction with simplified source location calculations, without the need for combined output power or signal cross correlation determinations. The size and shape of the array allows the use of simplified calculations as opposed to classical source location algebra which requires the solution of a set of simultaneous equations. Thus, in accordance with the method of the present invention, acoustic emission source direction and distance can be determined by making time delay measurements only, without the formulation of phase delays. Any distinct feature on the waveforms may be acquired at the four receiving units of the array, with the same feature being acquired at each, for source location determination. In accordance with the invention, the velocity of the selected wave feature is determined as a by-product of the source location procedure, and when the propagation characteristics of the plate-like structure are known, the distance to the emission source can be determined from each of the receiver elements independently.

When two sets of features common to the waveforms received at all four stations of the array are identified, two simultaneous direction estimates are obtained therefrom; no assumed wave velocities are required. Again, this measurement yields the group velocities of both features as a byproduct. The range, or distance to the source, is then found, using the average group velocities over the source to receiver distance measured.

High time resolution recording and processing circuits can be used to provide estimates of source distance. Since very short time intervals of measurement may be difficult to achieve, an alternative method of determining source distance may be used, wherein the time delay between different characteristics of a single waveform are measured. Thus, for example, the time delay between the first arriving modal peak of the wave and the second arriving modal peak is related to the source distance, and when this measurement is made at all array points, an accurate estimate of the source distance can be obtained. No absolute clock time measurement is required in accordance with this method, and the method is valid not only for plates but for plate-like structures such as shells and pipes.

BRIEF DESCRIPTION OF THE DRAWINGS

The foregoing and additional objects, features and advantages of the present invention will become apparent to those of skill in the art from the following more detailed consideration thereof taken in conjunction with the accompanying drawings, in which.

DESCRIPTION OF PREFERRED EMBODIMENTS

Figure 1:
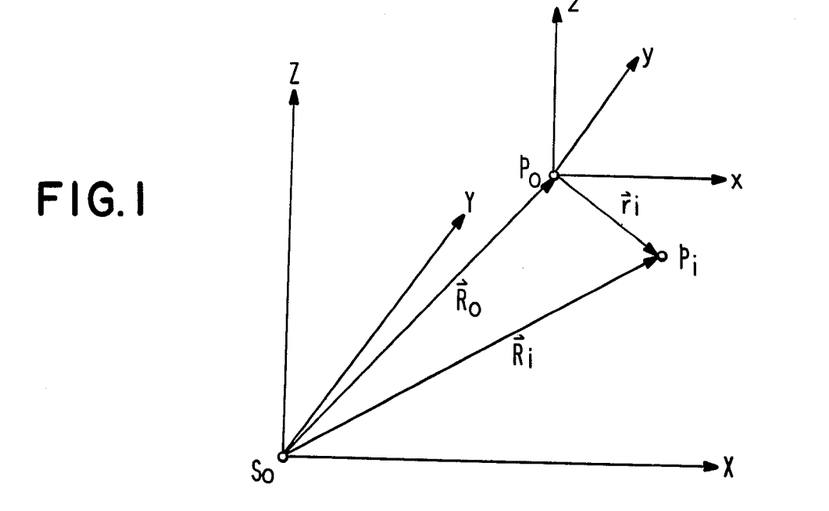
FIG. 1 is a diagrammatic illustration of the source and receiver array coordinate systems.

Turning now to a more detailed consideration of the present invention, a brief review of the theory of operation of the small transducer array will first be considered, with reference to the three dimensional coordinate system illustrated in FIG. 1. In this figure, the acoustic emission source is at the origin $S_o$ of an orthogonal coordinate system (X, Y, Z) with the receiving point $p_o$ being at the origin of a sensor element, or receiver, array coordinate system (x, y, z). The position vector of the receiver with respect to the source $S_o$ is identified as $R_o$, while other receiver points $p_i$ are denoted by the position vectors $r_i$ and $R_i$ with respect to the origins $p_o$ and $s_o$ respectively, the coordinates of receiver point $p_i$ being defined as $x_i$, $y_i$, $z_i$.

The relationships of the foregoing vectors can be written as follows:

$$\bar{R}_i = \bar{R}_o + \bar{r}_i \qquad (1)$$

$$\bar{R}_i \cdot \bar{R}_i = \bar{R}_i^2 = (\bar{R}_o + \bar{r}_i) \cdot (\bar{R}_o + \bar{r}_i) \qquad (2)$$

Performing the dot products in Eqn.(2) and defining $\delta_i$, $\alpha_i$, $\bar{u}_R$, and K to be:

$$\delta_i = R_i - R_o \qquad (3)$$

$$\alpha_i = (r_i^2 - \delta_i^2) \qquad (4)$$

$$\bar{u}_R = \bar{R}_o / R_o \qquad (5)$$

$$K = \tfrac{1}{2} R_o$$

one obtains:

$$\bar{r}_i \cdot \bar{u}_R + a_i K = \delta_i \qquad i=1, 2, \ldots N \qquad (6)$$

$$\bar{u}_R \cdot \bar{u}_R = 1. \qquad (7)$$

Applying the vector triangle-inequality to equation (1) and consequently to equation (4), the bounds for $\delta_i$ and $\delta_i$ are found as:

$$-r_i \leq \delta_i \leq r_i$$

$$(8)$$

$$0 \leq a_i \leq r_i$$

When a specific array geometry is chosen, all $\bar{r}_i$ are defined. Then $\delta_i$ can be calculated using the signals received at points $p_o$ and $p_i$ by measuring the relative arrival-time of the same acoustic wave feature whose speed, $c_o$, in the medium has previously been measured. If the absolute arrival times of signals at $p_o$ and $p_i$ is $T_o$, $T_i$ respectively, $\delta_i$ is given by, $$\delta_i = (T_i - T_o) C_o = \delta T_i C_o \qquad (9)$$

where $\Delta T_i$ is the relative arrival time at point $p_i$. Subsequently $\alpha_i$ is found by Eqn. (4). Noting that the unit direction vector $\bar{u}_R$ is given as:

$$\bar{u}_R = u_x \bar{i} + u_y \bar{j} + u_z \bar{k}, \qquad (9)$$

$$\vec{u}_R \cdot \vec{u}_R = u_y^2 + u_y^2 + u_z^2 = 1, \quad (10)$$

The unknowns in equations (6) are $u_x$, $u_y$ and $K$, since $u_z$ is given by equation (10). Accordingly, three of the N equations in (6) are sufficient for a mathematical solution, provided all three are linearly dependent. The linear dependency of equation (6) is determined by the choice of position vectors for the array points; that is, by the shape of the array. Considering a 4-point receiving array, equations (6) can be rewritten in matrix form, and the system of equations so obtained produce the following solutions $$u_x = (D_x + D_{xz} u_z) D_o^{-1} \quad (11)$$

$$u_y = (D_y + D_{yz} u_z) D_o^{-1} \quad (12)$$

$$K = (D_k + D_{kz} u_z) D_o^{-1} \quad (13)$$

with $$D_{kz} = \begin{vmatrix} x_1 & y_1 & z_1 \\ x_2 & y_x & z_2 \\ x_3 & y_3 & z_3 \end{vmatrix} \quad (14)$$

$$D_k = \begin{vmatrix} x_1 & y_1 & \delta_1 \\ x_2 & y_2 & \delta_2 \\ x_3 & y_3 & \delta_3 \end{vmatrix} \quad D_x = \begin{vmatrix} \delta_1 & y_1 & \alpha_1 \\ \delta_2 & y_2 & \alpha_2 \\ \delta_3 & y_3 & \alpha_3 \end{vmatrix} \quad D_y = \begin{vmatrix} x_1 & \delta_1 & \alpha_1 \\ x_2 & \delta_2 & \alpha_2 \\ x_3 & \delta_3 & \alpha_3 \end{vmatrix}$$

$$D_o = \begin{vmatrix} x_1 & y_1 & \alpha_1 \\ x_2 & y_2 & \alpha_2 \\ x_3 & y_3 & \alpha_3 \end{vmatrix} \quad D_{xz} = \begin{vmatrix} z_1 & y_1 & \alpha_1 \\ z_2 & y_2 & \alpha_2 \\ z_3 & y_3 & \alpha_3 \end{vmatrix} \quad D_{yz} = \begin{vmatrix} x_1 & z_1 & \alpha_1 \\ x_2 & z_2 & \alpha_2 \\ x_3 & z_3 & \alpha_3 \end{vmatrix}$$

where vertical bars denote a determinant and $u_z$ is the solution of the quadratic equation, $$(D_o^2 + D_{xz}^2 + D_{yz}^2) u_z^2 + 2(D_x D_{xz} + D_y D_{yz}) u_z + (D_x^2 + D_y^2 - D_o^2) = 0 \quad (15)$$

It is noted that there can be 0, 1 or 2 solutions given by the roots of equation (15), depending on the accuracy of the phase delays ($\delta_i$) measured at the receiving array, on the array coordinates, and on the particular location of the source of the acoustic emission with respect to the array. The solution of equation (15) is simple enough, but in practice is very much prone to errors, and small errors in the phase differences $\delta_i$ and in $\alpha_i$ are magnified since the solution contains the fourth power of almost all of the determinants involved. Such errors in $u_z$ directly affect the solutions for $u_x$, $u_y$ and K through equations (11), (12) and (13). However, these errors can be avoided by restricting the receiving array to lie on a plane by setting $z_i$ (i=1, 2, 3)=0. Then, $D_{xz}$, $D_{yz}$, and $D_{kz}$ are identically zero and the solution simplifies to:

$$u_x = -D_x/D_o \quad (16)$$

$$u_y = -D_y/D_o \quad (17)$$

$$2R_o = -D_o/D_k \quad (18)$$

where the $u_x$ and $u_y$ are the location coordinates of a receiver element given with respect to the receiver array coordinates and $u_z$ is given by equation (10). With such a simplification, the sign of $u_z$ is lost, thus introducing two possible Z coordinates. However, in practice this situation does not create problems since, as will be shown below, the source of acoustic emissions is known to be below the array, and $u_z$ can be interpreted accordingly.

Figure 2:
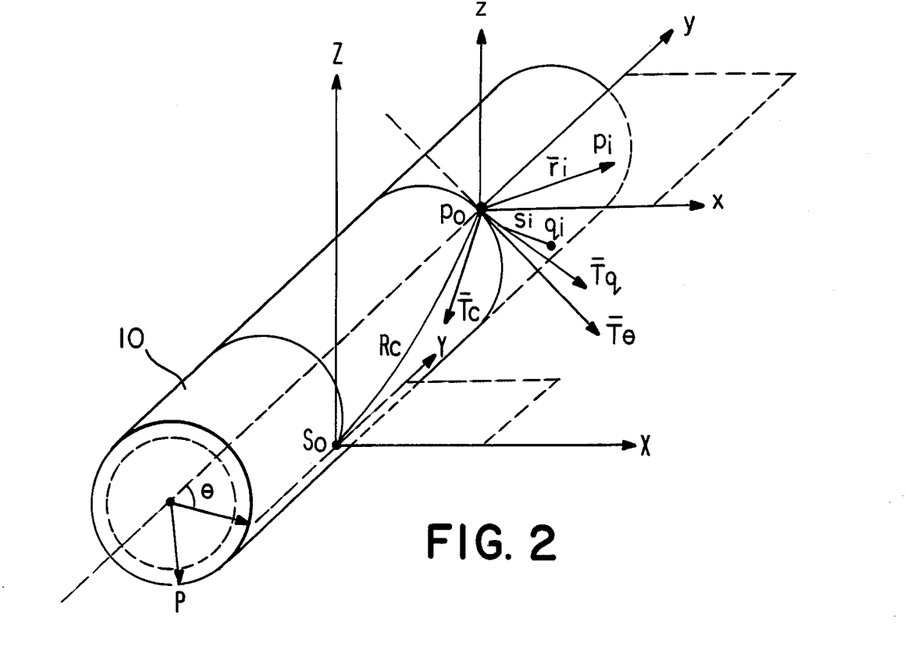
FIG. 2 is a diagrammatic illustration of the extension of the coordinate system of FIG. 1 to a cylindrical shell.

The equations (16), (17) and (18) can be used in source location applications in plates and plate-like structures where the curvature is small enough to assume that the $z_i$ coordinate is approximately zero. With proper interpretation, the solution is also valid in situations where the actual receiver points are on a developable cylindrical surface such as that of a shell or pipe. Such a case is shown in FIG. 2 wherein the axis of a circular cylindrical shell 10 is parallel to the y and Y axes of the receiver array and the source coordinates, respectively. As illustrated, the vectors $s_i$ and $R_c$ are the helical distances along the surface to receiver point $q_i$ and source point $S_o$, respectively, from point $p_o$. If the shell is cut along the y and Y axes, and is developed into a flat surface, the resultant planes (x, y) and (X, Y) will coincide. In the developed plane, the point $p_i$ corresponds to the point $q_i$ and accordingly the length of $s_i$ is equal to $r_i$, the tangent vector $\overline{T}_q$, which is tangent to $s_i$ at $p_o$ then coincides with the vector $\overline{r}_i$. Similarly, the tangent vector $\overline{T}_c$, which is tangent to the helical path $R_c$ at point $p_o$, will then coincide with the direction vector $\overline{u}_R$ in the plane. Consequently, it follows that circular paths on the shell diameter will develop as $p\theta = u_x R_o$, while the distances along the generator lines defined by the axes y, Y will remain unchanged. The helical paths will develop as $\sqrt{(p\theta)^2 + y^2} = R_o$. The problem then reduces to a source location problem on a plate where the shell array and source variables are transformed as:

$$s_i \to r_i; \quad \overline{T}_q \to \overline{r}_i / |\overline{r}_i| \quad (19)$$

$$\overline{T}_c \to \overline{u}_R; \quad R_c \to R_o \quad (20)$$

$$\overline{T}_\sigma \to \overline{u}_x; \quad \overline{u}_y \to \overline{u}_y \quad (21)$$

In the foregoing equations for determining source location on a plate or on a plate-like structure such as a shell or cylinder of large diameter, it is found that complete solutions for all parameters are not possible, thus leading to ambiguities which place certain restraints on the possible array configurations. Accordingly, when the source of acoustic emission is located either within or without the boundaries defined by the receiver elements of the array, the receiver element positions should be such that (1) all the receivers are not colinear; (2) the receivers do not form a circle having the source at its center; (3) no three receivers are colinear; and that (4) no pair of receivers lies on a straight line which is parallel to a straight line passing through the remaining pair of receivers. However, the last two restraints only apply if the source location is exterior to the region defined by imaginary lines joining the receiver element positions.

The sensitivity of the parameters $u_x$, $u_y$ and K to small deviations or measurement errors in the phase difference $\delta_i$ determines the errors to be expected in source location applications with a particular array. This sensitivity is defined by the gradients of the parameters with respect to the independent variables $\delta_i$, thus making it essential that all values of $\delta_i$ be measured as precisely as possible.

If a given receiver point is selected as the reference point, then the phase differences between the acoustic signal arriving at the reference and each of the remaining points will be defined as $\delta_1$, $\delta_2$ and $\delta_3$. Theoretically, when the three phase differences $\delta_1$, $\delta_2$, $\delta_3$ are known, the formulations given hereinabove will yield the source location vector; i.e., the direction to the source of emissions from the receiver point which is selected as a reference point. In practice, however, $\delta_i$ will never be exact, since arrival times of acoustic waveforms cannot be measured precisely. Uncertainties introduced by the propation speed measurement and uncertainties in the position vectors of the receiver elements will further compound the problem of precise measurement. In addition, the receiver elements, which in analysis are taken to be point receivers, in reality have finite dimensions; further, the source also has a finite dimension, and local perturbations in the geometry and material properties of the structure monitored create difficulties in measurement. Accordingly, it is apparent that the number of factors adverse to a correct source localization multiply rapidly.

To compensate for this situation, all possible sources of information from the array must be utilized. "Sign logic" is one such source available. By simply considering the algebraic signs of $\delta_i$ and all secondary differences formed by $\delta_i - \delta_j$, (where i is not equal to j) the source can be localized to a particular region which is much smaller than the area being monitored. Thus, spurious results obtained in the solution of the equations can immediately be discarded if the coordinates thus found are inconsistent with the localization obtained using sign logic data.

Given a set of phase differences $\delta_1$, $\delta_2$, $\delta_3$, where all are "signed" quantities, three other differences can be formed as follows:

$$\delta_4 = \delta_2 - \delta_1 \leq |\bar{r}_2 - \bar{r}_1| \quad (22)$$

$$\delta_5 = \delta_3 - \delta_1 \leq |\bar{r}_3 - \bar{r}_1|$$

$$\delta_6 = \delta_3 - \delta_2 \leq |\bar{r}_3 - \bar{r}_2|$$

This is a consequence of the fact that if four receiver points are taken in pairs combinations, each pair will give one difference which will locate the source point to the right or to the left of the midpoint which is perpendicular to an array line, according to whether the signed difference is positive or negative. Combining the information from all pairs, the region being monitored can be divided into subregions. The shape and size of these subregions depends completely on the geometry of the array vectors. In three dimensions, the subregions will be sub-volumes.

Figure 3:
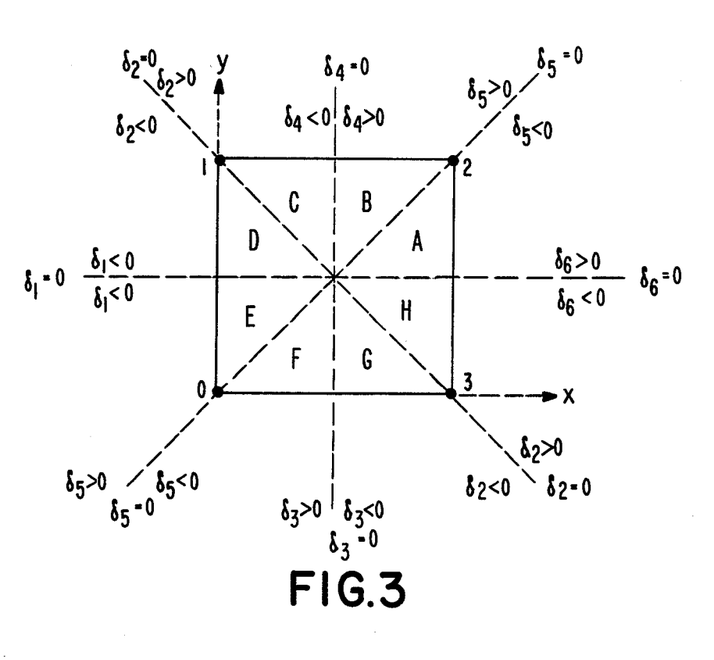
FIG. 3 is a diagrammatic illustration of sign logic regions for a square receiver array.

An example is given in FIG. 3 for a square array. As illustrated, the sign logic depends on which receiver is chosen as reference; in the example, the origin of the coordinates is taken to be this reference point, indicated at zero. As shown, the area is divided into 8 subregions, A-H, where each region has a unique combination of the signs six $\delta_i$'s. In practical applications, before the source location calculations are made in accordance with the preceding equations, this type of data is used to give a dependable localization of the source with respect to one of the subregions. Further, simple arithmetic will show that the secondary differences satisfy the equation:

$$\delta_4 + \delta_5 + \delta_6 = 0 \quad (23)$$

Equation (23) is particularly useful when statistical methods are used to estimate the time delays at the various receiver elements when the receive signals are noisy enough to require such treatment. If estimates of $\delta_1$, $\delta_2$, $\delta_3$, are made from measured data, secondary differences have to satisfy equation (23). An example of time delay estimation techniques using secondary differences and the condition given in equation (23) can be found in R. L. Curlin et al, "Improvement of Delay Measurements from Sonar Arrays via Sequential State Estimation", *Transactions IEEE on Acoustics, Speech and Signal Processing*, Part II of Three Parts, Special Issue on Time Delay Estimation, Vol. 1, ASSP-29, No. 3, 1981, pages 514-578.

There are three special cases of interest regarding the source location equations derived above. One instance is the form of the solution for finding source direction only, assuming that the distances $R_o$, $R_i$ (FIG. 1) are known or are estimated by some other means. A second case is the form of the solutions when the source is in the far-field of a small array so that $R_o$, $R_i$ are much larger than $r_i$. The final case concerns the choice of unit vectors ($\bar{r}_i/r_i$) such that the solutions for $u_x$, $u_y$, and $u_z$ uncouple for the two cases above.

In the first special case, where $R_o$ and $R_i$ are assumed to be known, the formulations given by equations 11, 12 and 13 are not necessary, and the source direction vector can be found by using equations (1) and (3) directly to obtain:

$$\bar{u}_r \cdot \bar{u}_i = \frac{\delta_i}{|\bar{r}_i|}\left[\frac{1}{2}\left(1 + \frac{R_i}{R_o}\right)\right] - \left[\frac{r_i}{2R_o}\right] \quad (24)$$

$$i = 1, 2, 3$$

$\bar{u}_i$ is the direction vector of an array point $p_i$ with respect to the origin point $p_o$. By judicious choice of $\bar{u}_i$, each of the three equations (24) above can be made to contain only of the unknowns $u_x$, $u_y$, $u_z$. Any orthogonal triad with its origin at $p_o$ will produce the desired result.

In the second special case, which involves far-field measurements, when a small array is used to monitor the exterior region, $R_o$, $R_i$ will always be larger than any of the $r_i$. Then equation (24) can be rewritten as:

$$\bar{u}_R \cdot \bar{u}_i \approx \delta_i/r_i \quad (25)$$

Thus, without estimating $R_o$ and resorting to the full solution of equations 11, 12 and 13, the source direction vector can be calculated. This approach also bypasses the ambiguities discussed above.

When the equation (25) is applied to source direction determination on a plate, the specific forms will be:

$$x_1\left(\frac{u_x}{c}\right) + y_1\left(\frac{u_y}{c}\right) \approx (T_1 - T_o) \quad (26)$$

$$x_2\left(\frac{u_x}{c}\right) + y_2\left(\frac{u_y}{c}\right) \approx (T_2 - T_o)$$

$$x_3\left(\frac{u_x}{c}\right) + y_3\left(\frac{u_y}{c}\right) \approx (T_3 - T_o)$$

where $T_o$, $T_i$ are the arrival times of the acoustic emission signals at the reference receiver $p_o$ and at the receiver $p_i$, respectively, time being measured with respect to some arbitrary reference. c is the velocity of any feature common to all signals in the acoustic wave, and preferably is the most conspicuous or easily identifiable feature. Even though two equations are sufficient in this application, it is preferred to use all three of the equations (26), using four receiver elements, but combining the first and third equations (26) as follows:

$$x_2\left(\frac{u_x}{c}\right) + y_2\left(\frac{u_y}{c}\right) \simeq (T_2 - T_o) \quad (27)$$

$$(x_1 - x_3)\left(\frac{u_x}{c}\right) + (y_1 - y_3)\left(\frac{u_y}{c}\right) \simeq (T_2 - T_3).$$

We then choose $x_1 = x_3$, $y_2 = 0$, and $y_3 = -|y_3|$ to obtain $$x_2\left(\frac{u_x}{c}\right) \simeq T_2 - T_o \quad (28)$$

$$(y_1 + |y_3|)\left(\frac{u_y}{c}\right) \simeq T_1 - T_3,$$

which simply gives, $$(u_x/c) = (T_2 - T_o)/x_2 = a$$

$$(u_y/c) = (T_1 - T_3)/(y_1 + |y_3|) = b \quad (29)$$

The a and the b are symbols to denote the RHS terms involving ($T_i$, $x_i$, $y_i$). When the source of acoustic emissions and the receiver array are on the same side of the plate (or shell) then $u_x^2 + u_y^2 = 1$. When they are on opposite sides, $u_x^2 + u_y^2 \simeq 1$, since propagation distance is much larger than the thickness of the plate. Accordingly, it can be shown that:

$$\frac{(u_x/c)}{\sqrt{(u_x/c)^2 + (u_y/c)^2}} = u_x = \frac{a}{\sqrt{a^2 + b^2}} \quad (30)$$

$$\frac{(u_y/c)}{\sqrt{(u_x/c)^2 + (u_y/c)^2}} = u_y = \frac{b}{\sqrt{a^2 + b^2}}$$

where $u_x$, $u_y$ are with respect to source coordinates and $$a = (T_2 - T_o)/x_2$$

$$b = (T_1 - T_3)/(y_1 + |y_3|). \quad (31)$$

The significance of result (30) together with equation (31) is that in the method of source location with a small array, where the source is in the exterior region, the source direction vector can be found without any reference to the velocity of the particular waveform feature which is common to all arriving signals and from which time differences to the various receiver elements are calculated. This means that any feature that appears on all wave forms and is clearly identifiable can be used to find the source direction. Experiments with the small transducer array have illustrated that accurate directional estimates can be obtained by this method even with relatively coarse time measurements on plate structures.

A further advantage of the small transducer array is that the group velocity of the waveform feature by which the direction is determined, as described above, takes the form:

$$c = \frac{1}{\sqrt{a^2 + b^2}} \quad (32)$$

If this velocity, c, is used to form the three phase delays as $$\delta_i = (T_i - T_o)\frac{1}{\sqrt{a^2 + b^2}} \quad (33)$$

$$i = 1, 2, 3$$

then the distance to the source is given as:

$$R_o = \tfrac{1}{2} \cdot D_o/D_k \quad (34)$$

where $D_o$ and $D_k$ are as in equation (14).

The foregoing relationship can be further developed so as not to use equation (34) if a second set of characteristic features on the signals being detected can be found. Then the group velocity of this second characteristic feature can also be calculated by the relationship given above, in addition to providing a second estimate of the direction vector. When this second feature is used, then the following two relationships are obtained:

$$c_1 = \frac{1}{\sqrt{a_1^2 + b_1^2}} \quad (35)$$

$$c_2 = \frac{1}{\sqrt{a_2^2 + b_2^2}}$$

With the two group velocities $c_1$ and $c_2$ obtained in accordance with equations (35) the source distance $R_o$ is given as:

$$R_o = \frac{\Delta T}{\sqrt{a_2^2 + b_2^2} \sqrt{a_1^2 + b_1^2}} \quad (36)$$

where $\Delta T$ is the time delay between the two different features on one and the same waveform. With this procedure, it is not possible to obtain a negative value for $R_o$, as often happens in using the full formulation, since $\Delta T$ and the difference in the denominator in equation (36) will have the same sign. With this approach, the ambiguities in the gradients of $R_o$ are also avoided.

It will be noted that the relationships described in equations (30) to (36) stem from the condition $U_x^2 + u_y^2 = 1$, which is exact if the source and the transducer array are located on the same side of the plate, or from the condition $u_x^2 + U_y^2 \simeq 1$, which is the case when the source is inside the plate or on the opposite surface of the plate. Therefore, these relationships will not provide a determination of source depth within the plate. However, this approach has the distinct advantage that a prior calibration of the acoustic emission system, or the assumption of a single velocity (either measured or computed) is not necessary. The present invention not only provides accurate measurements of direction, but in the course of obtaining directional measurements, group velocities are also found. Such an approach cannot be implemented with a large array since the apex angle formed by the lines joining array points to the source point is large, and this angle has a significant effect on the calculations outlined above.

Figures 4, 5:
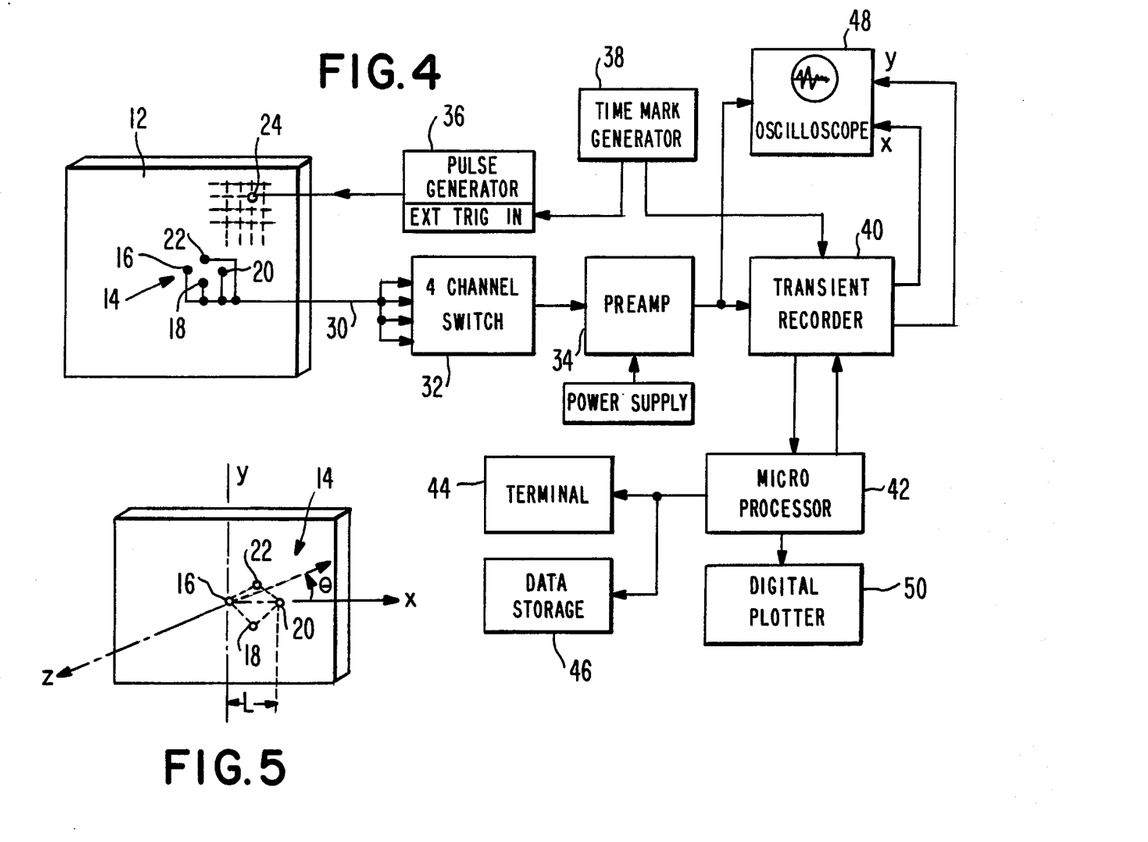
FIG. 4 is a diagrammatic illustration of an experimental circuit for determining the location of an acoustic emitter on a plate-like structure.
FIG. 5 is a detail of the plate-like structure of FIG. 4.

In an experimental test of the foregoing relationships, a simulated acoustic emission source was located on a flat solid plate 12 in the manner illustrated in FIGS. 4 and 5. A small transducer array 14 consisting of small, virtual-point receiver elements 16, 18, 20 and 22 is mounted on the top surface of the plate, with a source of acoustic emission 24 being located on the plate in a region exterior to the array vector boundaries, indicated by the dotted lines joining the transducer points in FIG. 5. As may be seen in FIGS. 4 and 5, receiver elements 16, 18, 20, and 22 of array 14 do not lie on a circle, and no three of them are colinear.

The choice of a small array is prompted by several considerations. One is that it is much easier to identify similarities in waveform structure on the acoustic signals if all the receiver elements are close together, since all four will be in the far or the near field of the source simultaneously. This allows better time-delay measurement, since identification of specific waveform characteristics is more accurate. A second factor is that with such an array, the time differences in arrivals will be sufficiently small that the observation of a single event will take place within a very short interval at all four stations, thereby reducing the possibility of recording multiple events as part of the same event. It should be noted that if two acoustic emission sources occur on the plate 12, and one is more than about 2L further from the array than the other, where L is the maximum array dimension, then all four receivers will receive the acoustic signal from one source before the signal from the other reaches the array.

In choosing a small array, the transducers to be used as the sensor elements, or receivers, will necessarily have to be extremely small in diameter so that they behave much like point receivers, as is assumed in the theoretical formulation given above. This small size also reduces the uncertainty in array point locations, as opposed to larger array applications where large diameter transducers receive signals over an average source-receiver distance, rather than an exact distance. The adverse effects of array-point location uncertainties in acoustic wave detectors is described in G. C. Carter, "Passive Ranging Errors Due to Receiving Hydrophone Position Uncertainty", *Journal of the Acoustic Society of America*, Vol. 65, No. 2, 1979, pages 528–530.

From a practical point of view, instead of applying four or more individual receiver elements to a plate or plate-like structure, a single unitary array with precisely imbedded receiver elements can be used. Such an arrangement further reduces transducer location uncertainties.

A further advantage of the small array arises from the dispersive nature of wave propagation in plate-like structures, where each feature, or mode, of the acoustic signal will travel with a different velocity. In prior large-dimensioned arrays, where precalibration measurements were required in order to obtain velocities of wave features, it has been found that unless the particular wave feature being measured is assigned the right velocity from the precalibration, major errors can result in locating the source. With the small array, on the other hand, the source location and group velocity of the feature can be obtained without prior calibration or velocity measurements.

In the experimental arrangement illustrated in FIG. 4, the received signals were analyzed using the relationships set forth hereinabove, and no particular feature or wave speed was predetermined. The feature that was chosen for measurement at the array for any particular source location was the one that was most easily and distinctly identifiable. The data was analyzed in view of the normal mode theory of plates under axisymmetric transient excitation in the far-field, as proposed by R. L. Weaver et al, "Axisymmetric Elastic Waves Excited by a Point Source in a Plate. Part I. Theory of Expansion in Normal Modes" and "Part II. Surface Responses", *Journal of Applied Mechanics*, 1981. This theory relates the source location parameters to various characteristic features of the response acquired at each of the receiver points. In the experiment, two types of source emitters were considered. One was a repetitive pulse using a piezoelectric transducer as the source, while the other was a step function produced by breaking a pencil lead against the plate. The repetitive source experiments were done with receivers and source on the same side of the plate, while the pencil lead source experiments were done on both sides, with the receiver array being on the top surface.

In designing the geometry of the small array 14 shown in FIGS. 4 and 5 the actual length of the array dimensions was determined by specifying a limit for the maximum time delay between the arrival of a wave feature at one and then another of the receivers. If the maximum characteristic dimension of the array is L, then the maximum time delay possible is given by:

$$L = c_p \Delta T_{max} \qquad (37)$$

If $c_p$, which is the P-wave speed of an acoustic emission, is taken to be about 0.5 cm per microsecond, then the above relationship (37) becomes:

$$\Delta T_{max.} = 2L \ \mu sec \qquad (38)$$

Since a small array is here used, such that:

$$\tfrac{1}{2} \leq L \leq 1.27 \ cm \qquad (39)$$

then:

$$1 \leq T_{max.} \leq 5 \ \mu sec \qquad (40)$$

Choosing the larger limits, the maximum characteristic dimension L of the array is taken as 2.54 cm. The other sides of the array are chosen to be smaller than L so as to be within the same limits.

The array vector directions are chosen in accordance with the equations (27), (28) and (29) set out above so that the estimates for $u_x$ and $u_y$ can be uncoupled with proper linear combinations of array vectors.

Referring again to FIG. 4, the plate 12 may be any suitable material. In one test, the plate was a glass plate of approximately one meter square; in another test, it was an aluminum plate of the same size. In actual monitoring situations, however, the plate may be any surface in which acoustic emissions are to be detected. For purposes of the experiment, a grid of lines parallel to the coordinate axes of the receiver array 14 was placed on the surface of the plate for purposes of identifying the various location points of the emission source. The array 14 was positioned with a selected transducer 16 placed at the center of the plate and at the origin of the x, y, z coordinates as illustrated in FIG. 5 to serve as the reference receiver. With this arrangement, negative as well as positive phase delays, $\delta_i$ are allowed.

In the form of the invention used in actual tests, the array receiver elements each had a diameter of 0.067 inch and a broad frequency response centered at about 1 MHz. All four receivers, 16, 18, 20 and 22 were embedded in a non-conducting matrix and were coupled to plate 12 by an ultrasonic coupling material. The outputs of the four transducers were each connected individually by way of a cable 30 and a four channel switch 32 to a preamplifier 34, to allow individual and sequential inspection of the received signals.

The repetitive pulse was provided as a simulated acoustic emission at acoustic source 24 by means of a 5-MHz, ¼ diameter ultrasonic p-wave transducer which was shock-excited by a pulse generator 36. Precise triggering of the pulse generator was supplied by an external time mark generator 38, which also supplied external trigger signals to a transient waveform recorder 40. The pulse generator was operated at a 10 ms repetition rate to avoid overlapping responses in the array at all locations and for consecutive triggers.

The transient recorder sampled the output of the preamplifier 34 at desired sampling intervals which may be set to, for example, 0.01, 0.02, 0.05, or 0.10 $\mu$sec, with the recorder sampling 2048 points in each interval. If signal averaging is preferred with the repetitive simulated pulse source, only 1024 points would be sampled, with every other point being acquired. This would reduce the resolution by essentially doubling the sampling intervals.

In the experiments conducted in accordance with the present invention, the sampling rate was set at 0.02 $\mu$sec for distances of up to 20H, where H is the thickness of the plate between the source and the array 14, and at 0.05 $\mu$sec for distances between 20H and 60H. Signals were averaged 100 times. For larger distances, the effective sample interval was 0.100 $\mu$sec.

The averaged signals were supplied to a microprocessor 42 and were digitized for display at a terminal 44, the microprocessor using conventional signal analysis software. The data so obtained was stored in a data storage 46 for later analysis, from which measured time delays $\delta_i$ were obtained for use in the equations for source location developed hereinabove. In addition, the signals received at the preamplifier 34 were fed to an oscilloscope 48 for display and the digitized signals were supplied to a digital plotter 50.

The results derived from such data acquisition illustrated that the signals received at all four transducer elements were very similar, and by careful examination of the signals, the same wave characteristic would be identified on each signal without difficulty. This identification of similar signals is enhanced as the source to receiver array distance increases. In this context there are two "far-field concepts". One is the "far-field" in terms of actual plate response where the source distance is large enough for the wave groups to form and to exhibit normal-mode structures. The other is the "far-field" of the small array 14 which starts as soon as the source distance is larger than the maximum characteristic array dimension. These similarities in signal structure reach an optimum when both the far-field conditions are satisfied simultaneously.

The determination of source location parameters from the signals acquired by the circuit arrangement of FIG. 4 follows the formulation developed hereinabove.

First of all, the transducer signals are examined to find one characteristic feature that is distinctly identifiable in each and every transducer response. Then the time of arrival of this feature with respect to some arbitrary reference time is measured on the display terminal 44, for example, by using digital cursors. These time measurements may then be recorded. It is not at all necessary to identify a first arrival, nor is it necessary to identify a named feature of the acoustic wave such as a "p-wave" or an "s-wave" or some other interpretable feature. All that is needed is that the same feature be identified in each response. The measured times are then substituted into equation (30) without converting them into phase delay calculations, and the direction vector components $u_x$, $u_y$ are then obtained directly.

Next, the velocity of propagation of the particular feature measured is calculated using equation (32). The velocity thus found is extremely meaningful, in the sense that it is an average velocity of propagation along the total length of the source-to-receiver path and thus is the proper velocity to use in formulating the phase delays. Another advantage of this approach is that as waveforms are received from all directions on the plate, variations in wave speed due to inhomogeneities of the plate can be measured, if desired.

With this velocity calculation and with the measured relative times ($T_j$), the appropriate phase delays $\delta_i$ are formed as given by equation (32) and the latter values are used in equation (34) for estimating the source distance. Note that the second variation of this approach, where two group velocities are calculated and used to determine source distance in accordance with equation (36) will be less sensitive to time difference measurement errors since it contains the same order terms in both the numerator and the denominator. Equation (34), on the other hand, contains $\delta_i$ terms in the denominator.

It was found in the test of this system that the accuracy of the $u_x$ and $u_y$ parameters is of the order of the sampling rate of the transient recorder. As indicated above, where the sampling interval is 0.04 microseconds for distances up to about 20H (plate thickness) and 0.100 microseconds for larger distances, the errors found were within this boundary, and were, in fact, closer to the 0.04 value. Thus, in the experiment, the absolute mean error in $u_x$ and $u_y$ was 0.037. It was further noted that direction determinations, within the above given values, was good for all ranges of direction and source distances considered in the experiment.

To confirm the accuracy of the present method, the group velocities determined by the relationships hereinabove were compared with measured p-waves and other mode velocities, and it was found that such measurements were within the boundaries of the sampling interval limits. However, it was found that with low sampling rates, some difficulties were encountered in obtaining consistent and reproducible distance determinations. A low sampling rate produces poor time resolution; that is, the time interval between measuring points does not allow for a sufficient number of digits to provide the required accuracy. Accordingly, a sampling rate of less than 0.01 microseconds is preferred for good accuracy in determining the source distance. However, the test showed the capability of the small transducer array to operate without precalibration or measured wave speed while obtaining close estimates of $u_x$, $u_y$ and c through relatively close time-delay measurements.

In the event that better resolution of source distance is required than can be obtained with a low sampling rate, the source direction process can be complemented by further analysis of the data to determine the source distance in view of the theory of normal modes of a plate. This theory has been discussed in the literature where it has been demonstrated that wave amplitudes of modes with maximum or minimum group velocities should appear particularly strong in recorded signals, and that the arrival associated with the first antisymmetric mode (A) is most conspicuous for both repetitive pulse source or step loading emissions. In addition, the dominant effect of various lowest modes have also been illustrated in the literature. Thus, if any pair of high intensity modes can be identified on experimental waveforms, the source distance can be computed by measuring their time delay and using their measured, or theoretically computed, modal group velocities.

In relating this type of analysis to the source location equations described hereinabove, which use an array of transducers, it may be found that the source-to-receiver distances of all the array points can be calculated by modal analysis; then using equation (24), the direction of the source can also be determined. Thus, all source location parameters can be determined, provided that two identical modes are identified at all four receiver points.

An analysis of the waveform data received in the above-described experiment revealed two distinct measurements that consistently appeared in all waveforms. One measurement is that the time delay between the first arriving modal peak and the second is given by $(2H/C_s) \pm 0.1$ $\mu$sec, where H is the plate thickness and $C_s$ is the shear wave speed. This feature is independent of source distance. The second observation was that the time delay in microseconds between the first peak and the largest amplitude later arriving peak is very close to the source-receiver distance in centimeters. This is the main feature in the waveforms that can clearly be related to source-receiver distance.

These observations indicate that if the group velocities of these two peaks can be ascertained experimentally and compared with theoretically computed counterparts, then one can write:

$$\frac{R_o}{c_2} - \frac{R_o}{c_1} = \Delta T_{12} \qquad (41)$$

where $R_o$ is the source to receiver distance, $\Delta T_{12}$ is the time delay between the peaks, and $c_1$ and $c_2$ are the group velocities of the first and late arrivals, respectively. This relationship gives:

$$R_o = \frac{c_1 \cdot c_2}{c_1 - c_2} \cdot \Delta T_{12} = f \Delta T_{12}$$

to yield the distance sought, where the factor f is designated as the product-to-difference quotient of speed in units of centimeters per microsecond.

In applying these equations to the experimental data obtained, it was found that the determination of source distance can successfully be obtained with the normal mode theory. This mode theory was extended to a plate-like structure such as shells and long pipes, and the applicability of the modal approach for source location was clearly apparent.

From the foregoing, it may be seen that a small array of transducers monitoring the exterior region to the array vectors can be used for locating acoustic emissions on plate-like structures without prior system calibration, and without prior velocity measurements or assumptions. Further, the information received by such a transducer array permits calculation of the source direction and distance by making time-delay measurements only, without the formulation of phase delays. Such determinations can be made using any distinct feature on the waveform, with that same feature being acquired at the four receiving units of the array. The group velocity of the feature taken is also determined as a by-product of the source location procedure. If two sets of such features common to all four waveforms received at the array stations can be identified, the determination is simplified and permits two simultaneous direction estimates to be obtained, at the same time yielding the group velocities of both the features. In both situations, only time delays are used, with no reference to a single or an assumed wave velocity. The range to the source is then found using these averaged group velocities taken over the source to receiver distance.

In conducting such measurements, a sampling interval in the range of 1 to 10 nanoseconds may be used to obtain a reasonable estimate of source distance. However, if such a sampling interval is not practically available in a measuring environment, the small array calculations can be complemented by determining the source distance using the theory of normal modes. The distance estimates made by this latter approach involve measurements on a waveform if only the reference distance is required. However, the distances to all array points can be found individually and this can in turn be used to provide the source direction. The normal mode analysis for source location is also extended to shells and long pipes, as is the small array calculation of source location.

In the system of the present invention, no absolute trigger or clock time is required in acoustic emission source location. Using a combination of modal analysis and small array calculations, the direction vector components and the group velocities can be obtained to accuracies within time measurement device timing intervals.

Although the present invention is disclosed in terms of preferred embodiments, it will be apparent that numerous variations and modifications can be made without departing from the true spirit and scope thereof, as set forth in the following claims:

We claim:

1. A small transducer array for omnidirectional monitoring of acoustic waves on a plate-like surface, comprising:
   a surface to be monitored;
   four substantially point receiver transducers acoustically coupled to said surface, each transducer being adapted to produce an output signal corresponding to received acoustic waves on said surface, said transducers forming an array on said surface wherein no three transducers are colinear, wherein said transducers do not lie on a circle, and wherein no two of said four transducers lie on a straight line which is parallel to the direction of a straight line passing through the remaining two transducers, said transducer array having a maximum dimension that is less than or on the order of the wavelength of the acoustic waves be monitored;
   circuit means responsive to output signals from said transducers for determining the location of the source of received acoustic waves, said circuit means including:

means for determining the time difference at each of said transducers between the arrival of a first selected characteristic feature of said acoustic waves and the arrival of a second selected characteristic feature of said acoustic waves;

means for determining from said time difference the distance from the transducers to the source of received acoustic waves;

means for determining the time delays between the arrival of any selected characteristic wave feature at a first of said transducers and each of the remaining three transducers; and means for determining from said time delays, the direction of the source of the received acoustic waves with respect to the transducers.

2. The small transducer array of claim 1 wherein said circuit means further includes means for determining the group velocity of said any selected characteristic feature of said acoustic waves from said measured time delays.

3. The small transducer array of claim 1, wherein said acoustic waves on said plate-like surface are generated by a source outside the boundaries of said array.

4. The small transducer array of claim 1, wherein each of said transducers is a piezoelectric transducer having a diameter of about 0.067 inch.

5. The small transducer array of claim 4, wherein the ratio of the minimum separation between transducers in said array to the radius of a single transducer is approximately 17.

6. The small transducer array of claim 1, wherein said circuit means includes waveform recorder means and switch means for selectively connecting the output signals from each of said transducers to said waveform recorder means, and wherein said waveform recorder samples and averages each of said received output signals.

7. The small transducer array of claim 6, wherein said circuit means further includes microprocessor means for determining said time delays and said time difference, and from said time delays and time difference, the direction and distance of the source of said received acoustic signals from said transducer array.

8. The small transducer array of claim 1, wherein the maximum spacing between any two of said transducers is approximately 1 inch.

9. The method of determining the location of a source of acoustic emissions on a plate-like surface, comprising:

acoustically coupling four substantially point receiver transducers to a surface to be monitored, said transducers forming an array on said surface wherein no three transducers are colinear, wherein said transducers do not lie on a circle, and wherein no two of said four transducers lie on a straight line which is parallel to the direction of a straight line passing through the remaining two transducers;

measuring the time of arrival of a selected characteristic feature of an acoustic wave traveling on said surface at each of said transducers;

determining the time delay between the arrival of said selected characteristic feature at a reference transducer in said array and the arrival of the same selected characteristic feature at each of the remaining three transducers, determining from said time delay measurements the direction of the source of acoustic emissions producing said acoustic wave with respect to said reference transducer;

determining from said time delay measurements the velocity of propogation of said selected characteristic feature; determining from said velocity of propagation and said time delay measurement, the three phase delays of said selected characteristic feature between said reference transducer and each of said three remaining transducers; and, determining from said phase delays the distance from said reference transducer to said source of acoustic emissions.

10. The method of claim 9, wherein the step of determining said time delays comprises sampling the acoustic wave arriving at each of said transducers;

identifying a characteristic feature of said acoustic wave common to each transducer; and for a repetitive source, averaging the sampled acoustic wave signals corresponding to the identified characteristic feature at each transducer.

11. The method of claim 9, wherein said transducers are coupled to a surface to be monitored so that the maximum spacing between any two of said transducers is approximately 1 inch.

12. The method of determining the location of a source of acoustic emissions on a plate-like surface, comprising:

acoustically coupling four substantially point receiver transducers to a surface to be monitored, said transducers forming an array on said surface wherein no three transducers are colinear, wherein said transducers do not lie on a circle, and wherein no two of said four transducers lie on a straight line which is parallel to the direction of a straight line passing through the remaining two transducers;

measuring the time of arrival of a first selected characteristic feature of an acoustic wave traveling on said surface at each of said transducers;

measuring the time of arrival of a second selected characteristic feature of an acoustic wave traveling on said surface at each of said transducers;

determining from the difference in the arrival times of said first and second selected characteristic features, and from the determined group velocities of said first and second selected characteristic features, the distance from said transducers to said source of acoustic emissions;

determining the time delays between the arrival of any selected characteristic feature at a reference transducer in said array and the arrival of the same selected characteristic feature at each of the remaining three transducers; and, determining from said time delay measurements the direction of the source of acoustic emissions with respect to said reference transducer.

13. The emthod of claim 12 wherein said first selected characteristic feature is the first arriving modal peal of the acoustic wave generated by said source of acoustic emissions, and said second selected characteristic feature is the largest amplitude later arriving modal peak of said acoustic wave.

14. The method of claim 12 wherein the step of determining from said time delay measurements the direction of said source of acoustic emissions includes;

determining the three phase delays of said any selected characteristic feature between said reference transducer and said three remaining transducers; and, determining from said phase delays the direction vector for said source of acoustic emissions.

15. The method of claim 12 wherein the step of determining said time delay comprises sampling the acoustic wave arriving at each of said transducers;

identifying a characteristic feature of said acoustic wave common to each transducer; and for a repetitive source, averaging the sampled acoustic wave signals corresponding to the identified feature at each transducer.

16. The method of claim 12 wherein the step of determining the distance from said transducers to said source of acoustic emissions includes determining the time delays between the arrival of said first and second characteristic features at a reference transducer in said array and the arrival of said first and second characteristic features at each of the remaining three transducers; and determining from the time delay measurements of said first and second characteristic features, the group velocities of said first and second characteristic features.

17. The method of claim 12, wherein said transducers are coupled to a surface to be monitored so that the maximum spacing between any two of said transducers is approximately 1 inch.

* * * * *